(12) United States Patent  
Kaye et al.

(10) Patent No.: US 7,967,744 B2
(45) Date of Patent: Jun. 28, 2011

(54) BIOPSY INLET VALVE (75) Inventors: Christopher J. Kaye, Concord, OH (US); Dean J. Secrest, Concord, OH (US)

(73) Assignee: U.S. Endoscopy Group, Inc., Mentor, OH (US)

( * ) Notice: Subject to any disclaimer, the term of this patent is extended or adjusted under 35 U.S.C. 154(b) by 1083 days.

(21) Appl. No.: 11/784,949

(22) Filed: Apr. 10, 2007

(65) Prior Publication Data

US 2007/0282168 A1    Dec. 6, 2007

Related U.S. Application Data (60) Provisional application No. 60/790,721, filed on Apr. 10, 2006.

(51) Int. Cl.
*A61B 1/00* (2006.01)
*A61M 5/178* (2006.01)

(52) U.S. Cl. ............... 600/154; 604/167.01; 604/167.06
(58) Field of Classification Search .................. 600/154; 604/167.01–167.06
See application file for complete search history.

(56) References Cited

U.S. PATENT DOCUMENTS

| | | | |
|---|---|---|---|
| 4,198,958 A | | 4/1980 | Utsugi |
| 4,240,411 A | * | 12/1980 | Hosono .......................... 600/154 |
| 4,412,531 A | | 11/1983 | Chikashige |
| 4,572,163 A | | 2/1986 | Collins et al. |
| 4,653,477 A | | 3/1987 | Akui et al. |
| 4,715,360 A | * | 12/1987 | Akui et al. ..................... 600/154 |
| 4,736,732 A | | 4/1988 | Shimonaka et al. |
| 5,234,417 A | * | 8/1993 | Parks et al. .................... 604/533 |
| 5,247,966 A | | 9/1993 | Stevens et al. |
| 5,324,254 A | | 6/1994 | Phillips |
| 5,697,888 A | | 12/1997 | Kobayashi et al. |
| 5,725,478 A | | 3/1998 | Saad |
| 5,800,493 A | | 9/1998 | Stevens et al. |
| 5,891,014 A | | 4/1999 | Ariba |
| 5,971,917 A | | 10/1999 | Komi et al. |
| 6,117,070 A | * | 9/2000 | Akiba ........................... 600/154 |
| 6,126,592 A | | 10/2000 | Proch et al. |
| 6,126,633 A | | 10/2000 | Kaji et al. |
| 6,383,132 B1 | | 5/2002 | Wimmer |
| 6,569,087 B2 | | 5/2003 | Naito et al. |

(Continued)

OTHER PUBLICATIONS

Office Action from U.S. Appl. No. 11/137,636 dated Jan. 30, 2009.

(Continued)

*Primary Examiner* — Linda C Dvorak
*Assistant Examiner* — Alireza Nia
(74) *Attorney, Agent, or Firm* — Calfee Halter & Griswold LLP (57) ABSTRACT A valve for use in irrigating, accessing and sealing the instrument channel of an endoscope is disclosed. The valve is adapted for installation onto an endoscope instrument inlet port. The valve includes a body, a flip cap, and a seal curtain. The body has an open end adapted for connection to the inlet port, interior walls defining an cavity, and an outer surface defining a valve entry port. The entry port is connected to a channel open to the cavity. The flip cap is removably connectable to the valve entry port and has a slit therethrough. The seal curtain contains a flexible cylindrical portion, and a lid at one end, and is removably insertable into the cavity. A longitudinal axis of the seal curtain in an installed position within the cavity is at an angle with respect to a longitudinal axis of the body.

21 Claims, 10 Drawing Sheets

U.S. PATENT DOCUMENTS

| | | | |
|---|---|---|---|
| 6,666,818 B2 | 12/2003 | Dhindsa | |
| 6,808,521 B1 * | 10/2004 | McMichael | 604/533 |
| 7,220,226 B2 * | 5/2007 | Rovegno | 600/104 |
| 7,226,411 B2 | 6/2007 | Akiba | |
| 2003/0069549 A1 | 4/2003 | MacMahon et al. | |
| 2005/0027165 A1 | 2/2005 | Rovegno | |
| 2005/0267417 A1 | 12/2005 | Secrest et al. | |

OTHER PUBLICATIONS

International Search Report and Written Opinion from International Application No. PCT/US07/08947, dated Dec. 26, 2007.

Office Action from U.S. Appl. No. 11/137,636 dated Aug. 22, 2008.

* cited by examiner

BIOPSY INLET VALVE

CROSS-REFERENCE TO RELATED APPLICATIONS

This non-provisional application claims the benefit of U.S. Provisional Patent Application No. 60/790,721, entitled "Biopsy Inlet Valve," filed Apr. 10, 2006, the entire disclosure of which is incorporated herein by reference, to the extent that it is not conflicting with this application.

FIELD OF THE INVENTION

The present invention relates to valves and to a biopsy inlet valve for use with the instrument channel inlet port of an endoscope.

BACKGROUND OF THE INVENTION

Endoscopes are well-known in the art and are commonly used for numerous medical procedures that involve intubation of the esophagus and gastro-intestinal tract. As such, many devices and accessory instruments have been developed that relate to the operation of an endoscope. One such device well-known in the endoscopic art field is commonly referred to as a biopsy channel inlet valve, or BCIV.

A BCIV is used to provide sealable access to the accessory instrument channel of an endoscope. In the beginning of an exemplary endoscopic procedure, the body cavity or lumen is insufflated to provide a lumen for visualization and insertion of an accessory instrument. In doing so, a positive pressure is created in the body and in the channel. The pressure is then retained or held back by use of a BCIV. Further, the valve is required to seal off an instrument passing into and through the channel. At the end of the procedure, the instrument is removed. A biopsy valve is designed with internal ridges to squeegee blood and other body fluids from the outer surface of an instrument as it is removed from the channel.

During use of these instruments, a need typically arises to irrigate the internal work site and sometimes, also the instrument channel itself. A physician's view of the internal work site can be clouded by various body fluids or debris. A clear view is important for a successful procedure. Conventionally, doctors have removed the accessory instrument, inserted a blunt instrument such as a syringe through a valve sealing an inlet port to the channel and merely sprayed water down the channel. This method has created several problems, such as for example, the valve becomes damaged, the accessory instrument must be removed during irrigation to prevent damage, and undesired time is added to the overall length of the endoscopic procedure. Further, existing valves require manual cleaning between use for disinfection.

The present invention is an improved valve for providing irrigation of the instrument channel of an endoscope. The valve provides sealable access to an inlet port of the instrument channel, is not susceptible to damage during endoscopic procedures, has increased durability over prior art designs, does not require the removal of the accessory instrument during irrigation, and reduces the time of the overall endoscope procedure by permitting remote irrigation access by a doctor or assisting nurse.

The device is made of a relatively inexpensive flexible plastic. Consequently, the device is effectively disposable after one use which eliminates the need to manually clean, flush, and dry existing valves, the threat of cross-contamination from stored valves, and the requirement for disinfection in general. Further, the risk of health worker exposure to infectious body fluid is reduced by eliminating the use of reprocessed valves that are in poor condition and susceptible to leaking

SUMMARY OF THE INVENTION

In an illustrated embodiment of the invention, a valve for providing resealable access to the instrument channel of an endoscope includes a body having an open end adapted for connection to the endoscope instrument inlet port, an internal cavity, and a valve entry port. A flip cap is removably connectable to the valve entry port. Within the cavity, a seal curtain having a flexible cylindrical portion is inserted such that a longitudinal axis of the seal curtain in an installed position within the cavity is at an angle with respect to a longitudinal axis of the body. The valve installed on the instrument port directs fluids exiting the instrument port in a direction of the cylindrical member Further features and advantages of the invention will become apparent from the following detailed description made with reference to the accompanying drawings.

BRIEF DESCRIPTION OF THE DRAWINGS

FIG. 2b is a cross-sectional view of the seal curtain of FIG. 2a;

FIG. 2c is a perspective view of the seal curtain of FIG. 2a;

FIG. 10b is a plan view of the valve of FIG. 10a;

FIG. 10c is a photograph of a valve having similar features as the valve of FIG. 10a;

FIG. 12b is a top view of the valve of FIG. 12a;

FIG. 14b is a cross-sectional view of the sealing device of FIG. 14a; and

DESCRIPTION OF THE INVENTION

The Detailed Description of the Invention merely describes preferred embodiments of the invention and is not intended to limit the scope of the specification or claims in any way. Indeed, the invention as described by the claims is broader than and unlimited by the preferred embodiments, and the terms in the claims have their full ordinary meaning.

Figures 1A, 1B:
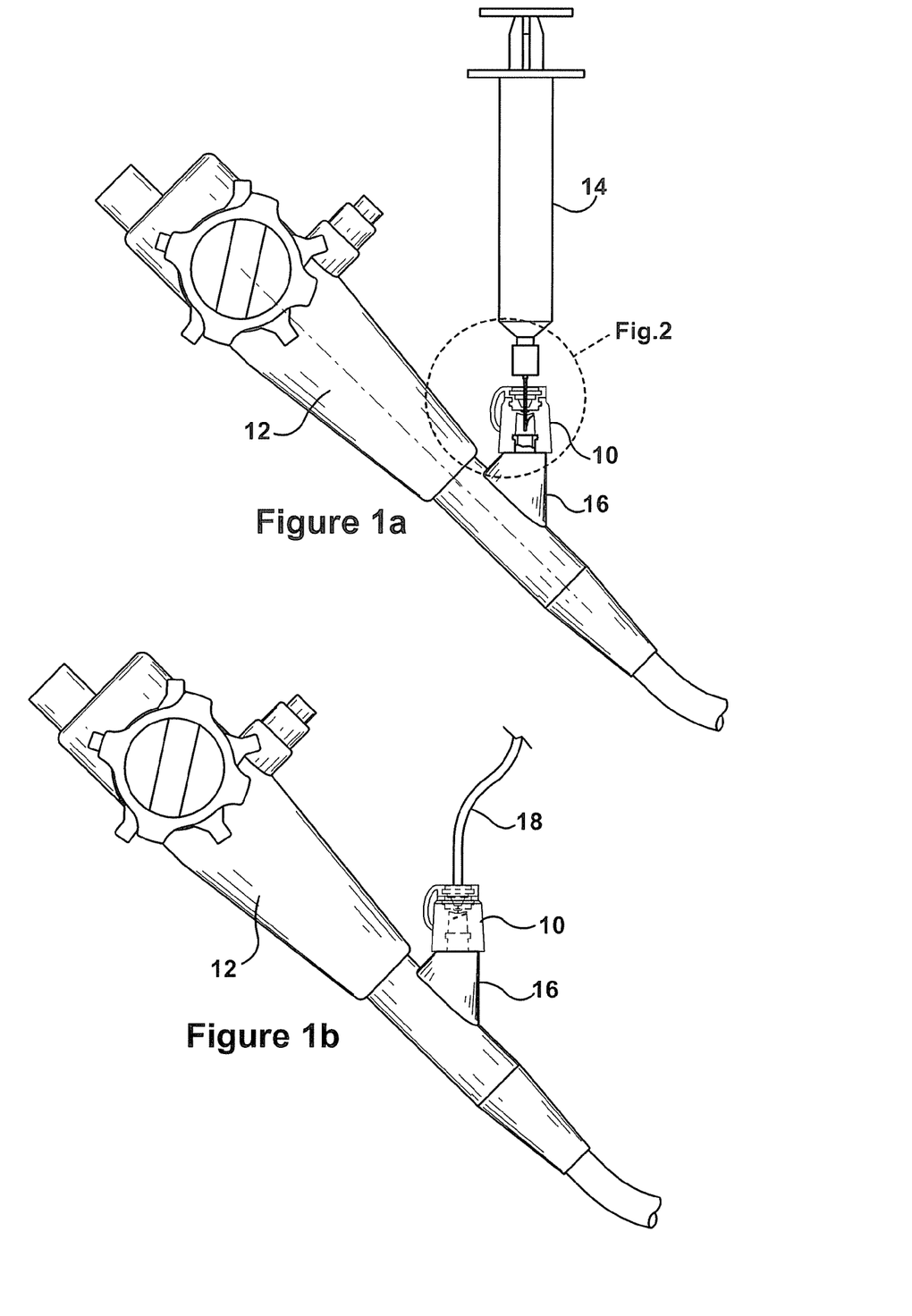
FIG. 1a is a plan view of a biopsy inlet valve shown in use installed on an endoscope.
FIG. 1b is a plan view of the valve of FIG. 1a, showing the valve in use during an endoscopic procedure.

Referring now to the drawings, FIG. 1a is a plan view of an irrigation biopsy inlet valve 10. A valve of this structure is shown and described in U.S. patent application Ser. No. 11/137,636, entitled "Irrigation Biopsy Inlet Valve," filed on May 25, 2005, the entire disclosure of which is incorporated herein by reference, to the extent that it is not conflicting with this application.

The valve 10 is used to provide sealable access to an instrument channel of an endoscope 12. The valve 10 is designed to connect to an instrument inlet port 16 of the endoscope 12. FIG. 1b is another plan view of the valve illustrated in FIG. 1a, showing the valve in use during an irrigation procedure. An endoscopic instrument 18 is shown inserted through the valve 10. As shown in FIG. 1, a common 60 cc syringe 14 or the like can be used by an operator to flush fluids through the instrument channel of the endoscope 12 in order to cleanse the body lumen.

Figure 1C:
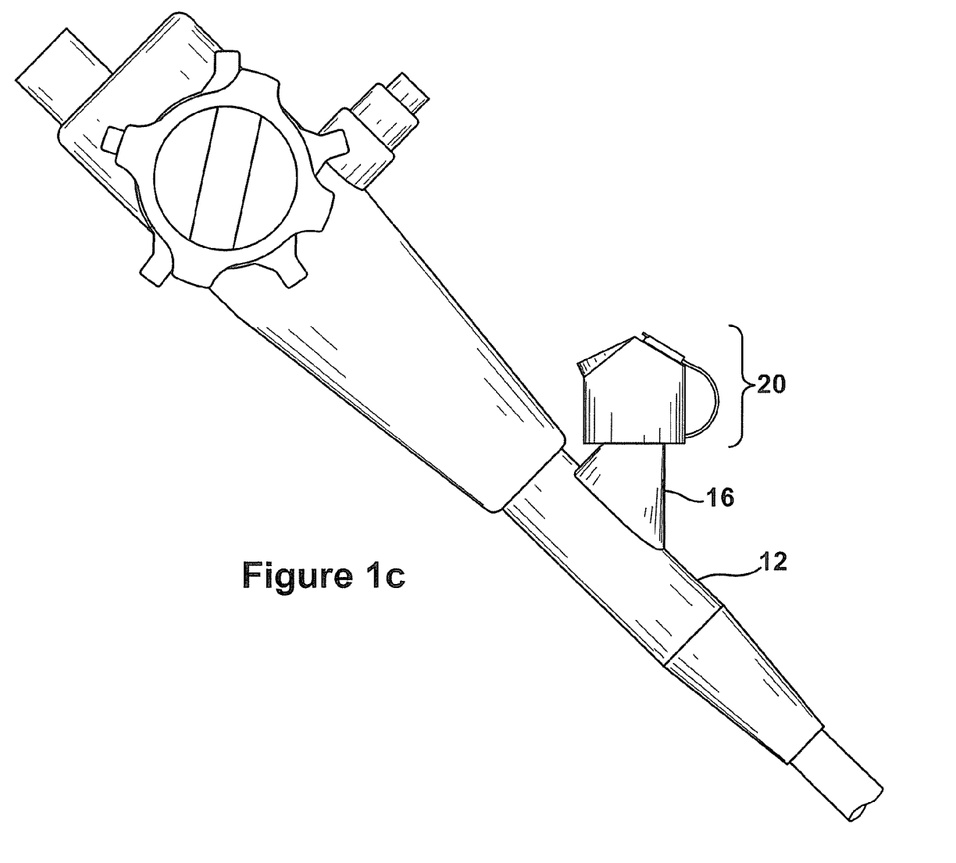
FIG. 1c is a photograph of a valve having a generally Y-shaped internal cavity.

FIG. 2 is a photograph of an embodiment of the invention. A valve 20 is shown installed onto an instrument inlet port 16 of an endoscope 12. The valve is designed to proved a seal of the inlet port 16 and allow a user to install and remover endoscopic instrument, and irrigate the internal instrument channel (not shown) of the endoscope 12, each without removing the valve 20 from the port 16.

Figure 2A:
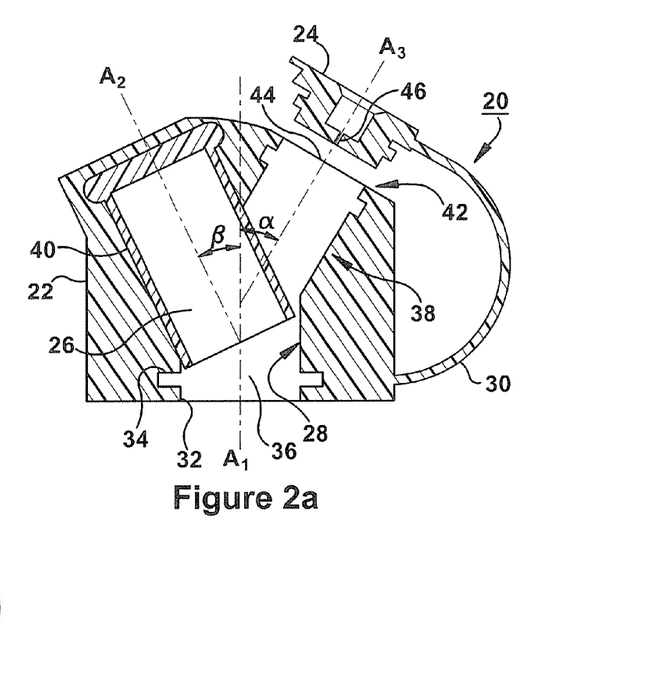
FIG. 2a is a cross-sectional view of the valve of FIG. 1c, showing a seal curtain and an outlet port at an open end that are not co-axial.

A cross-sectional view of the valve 20 is shown in FIG. 2a. The valve is highly adaptable for use in a stored or capped position, to allow access by an instrument, or for irrigation of the endoscope instrument channel. It should be understood by those with ordinary skill in the art that a wide variety of endoscopic instruments can be used in the practice of the present invention, such as for example, snares, retrieval nets or forceps. It should also be understood by those with ordinary skill in the art that a wide variety of irrigation sources can be used in the practice of the present invention, such as for example, an electric water pump with a foot control switch.

The valve 20 includes a body 22, a flip cap 24 and a seal curtain 26. The seal curtain is insertable into a cavity 28 defined by the inner walls of the body. The flip cap 24 is held to the body by a tether 30. As shown, the body 22, cap 24 and tether 28 are integrally molded.

The cavity is exposed at an open end 32 of the body. An annular rim 34 adjacent the open end is sized for mating with a ridge on the exterior portion of a conventional instrument inlet port 16. The cavity 28 of the body is generally Y-shaped having a main branch 36 leading to the open end 32 and two secondary branches. The first secondary branch 38 is toward a valve entry port 44 and a second secondary branch 40 in which the seal curtain 26 is installed. To be discussed later in greater detail, this orientation directs fluids exiting the instrument inlet port 16 in a direction toward the seal curtain 26.

An outer surface 42 of the body 22 defines a valve entry port 44. The relatively large bore 44 would allow easy access of devices to be inserted in the cavity. The flip cap 24 is removably connectable to the valve entry port. As shown in the Figures, the flip cap has a slit therethrough 46. The slit 46 permits the insertion of various devices, such as for example, a guidewire at the beginning of an endoscopic procedure, needles, and irrigation tubes.

Figure 2B:
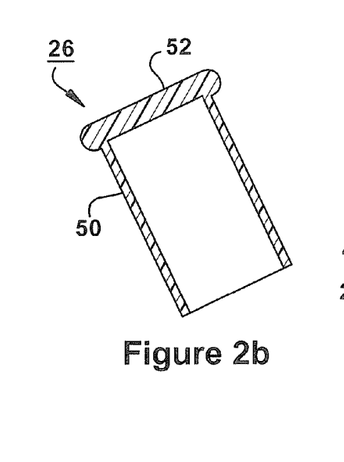
Figure 2C:
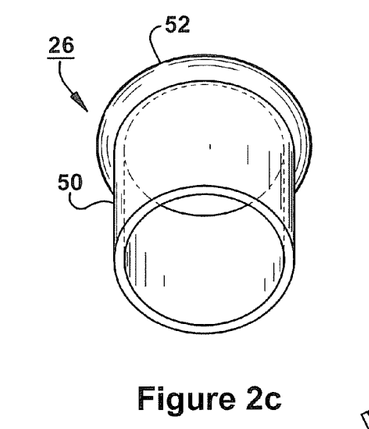

FIG. 2b is a cross-sectional view of the seal curtain illustrated in FIG. 2a. The seal curtain 26 is a component that is inserted into the cavity 28 and provides additional sealing of the endoscope instrument channel, above and beyond the slit in the cap that would remain closed for the majority of the procedure. As shown, the seal curtain is inserted through the open end 32 of the body 22. The seal curtain may be a flexible injection molded plastic component. The seal curtain has a flexible cylindrical portion 50 and a lid 52 at one end. In the inserted position shown in FIG. 2a, the lid is distal from the open end. A bottom perspective view of the seal curtain 26 is shown in FIG. 2c.

As shown in FIG. 2a and others, the three main valve components are positioned relative to each other in a confined and distinct relationship. The outlet port of the body 20 defines a longitudinal axis $A_1$ that is neither co-axial nor parallel with a longitudinal axis $A_2$ defined by the seal curtain in an installed position in the body. Further, the outlet port of the body 20 defines an axis $A_1$ that is neither co-axial nor parallel with a longitudinal axis $A_3$ defined by the inlet port of the body. It is believed this positioning of the inlet port, outlet port, and seal curtain maximizes valve performance and minimizes valve size.

Still referring to FIG. 2a, the inlet port 44 of the body 22 defines a longitudinal axis $A_3$ which is oriented at an angle α with respect to $A_1$. Fluid may be dispensed through the inlet end in a direction toward the endoscope. A syringe may be inserted through the flip cap aperture 46 to irrigate an instrument channel of the endoscope. It is believe that an angle α of less than 90 degrees promotes flow down the instrument channel and generally improves irrigation. Other irrigation apparatus may be connected to the check valve in the practice of the present invention.

The longitudinal axis $A_2$ of the seal curtain 26 is oriented at an angle β with respect to $A_1$. It is believe that an angle β of between 0 and 90 degrees promotes flow of fluid exiting the instrument inlet port 16 in a direction into the cylindrical portion 50. In one embodiment, angle β is equal to angle α. It should be appreciated by others with ordinary skill in the art that the angle β may be equal to, greater than, or less than, the angle α in the practice of the present invention.

Figure 3:
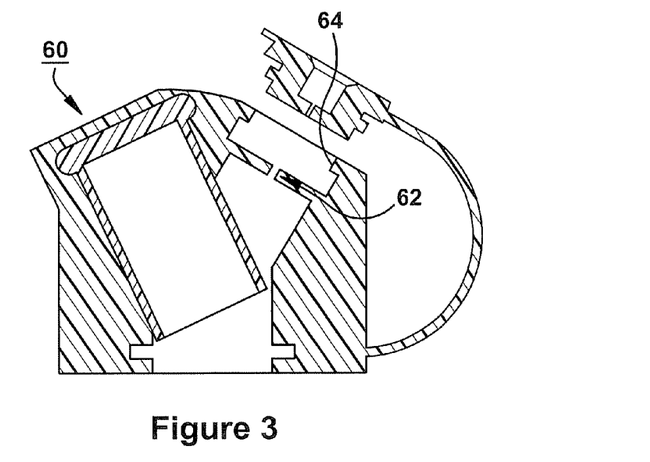
FIG. 3 is a cross-sectional view of a valve having a small diameter membrane at a valve inlet port.

FIG. 3 is a cross-sectional view of a valve 60 having a small diameter membrane 62 at a side inlet port 64. The small hole in the center of the membrane 32 helps minimize the fluid path when small endoscopic devices are used and the thin membrane can flex and desirably deform out of the path of larger endoscopic devices.

Figure 4:
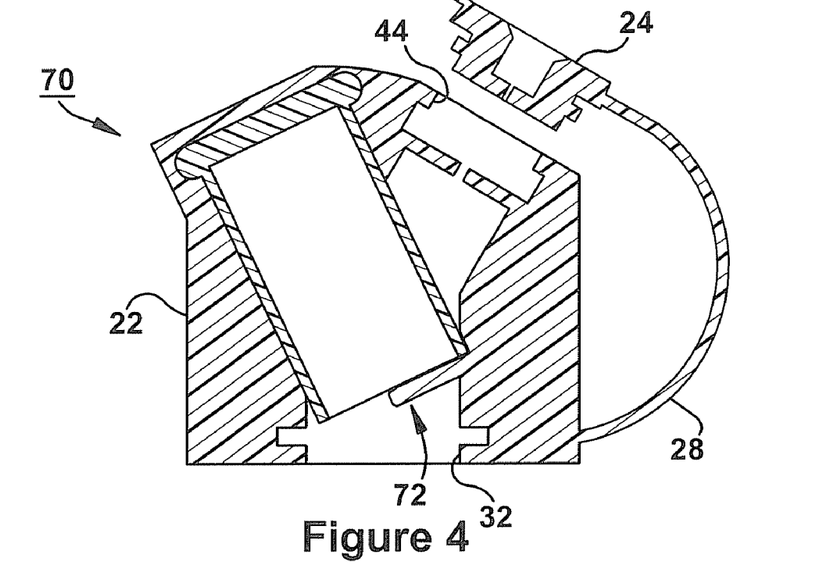
FIG. 4 is a cross-sectional view of a valve having an internal flap member.

Another embodiment of the invention is shown in FIG. 4. A cross-sectional view of a valve 70 having an internal flap member 72 is shown. The flap member 42 inhibits fluid movement in a direction from the open end 32 to the inlet port 44.

Figure 5:
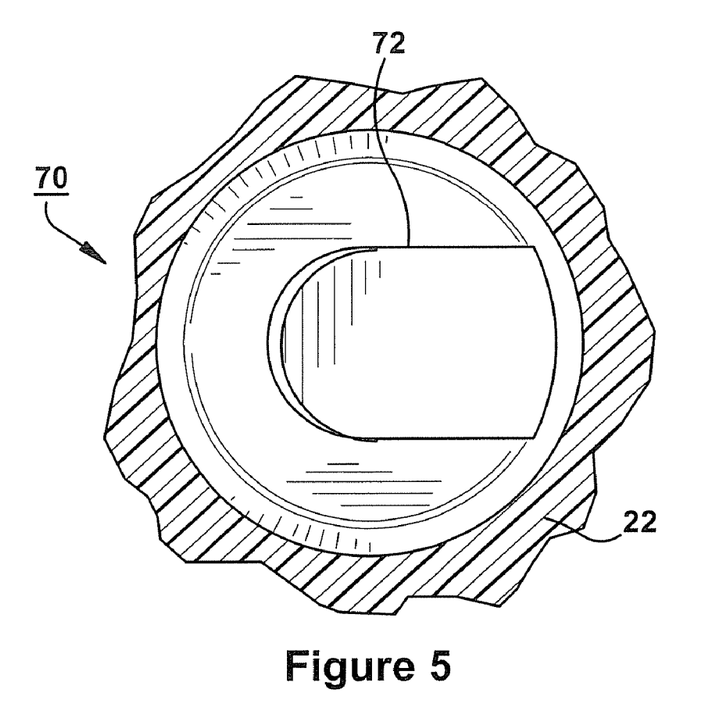
FIG. 5 is a partial cross-sectional bottom view of the valve of FIG. 4, showing the internal flap member from the perspective of the open end of the valve.

The flap member 42 is integrally molded with the valve body 22 and extends across the access channel to the endoscope. This position acts as a wiper that further inhibits the direct flow of fluids up and out of the inlet end of the valve. It also helps keep the inserted instrument (not shown) in intimate contact with the seal curtain 26, which is believed to improve the effectiveness of the curtain and the flap member. In another embodiment, the flap member may be adjacent to the inserted seal curtain to provide resistance against the seal curtain moving out of position during operation. As shown, the tether 28, flip cap 24, body 22 and flap member 72 are one integral piece constructed of flexible plastic. A cross-sectional bottom view of the internal flap member 72 from the perspective of the open end of the valve 70 is shown in FIG. 5.

Figure 6:
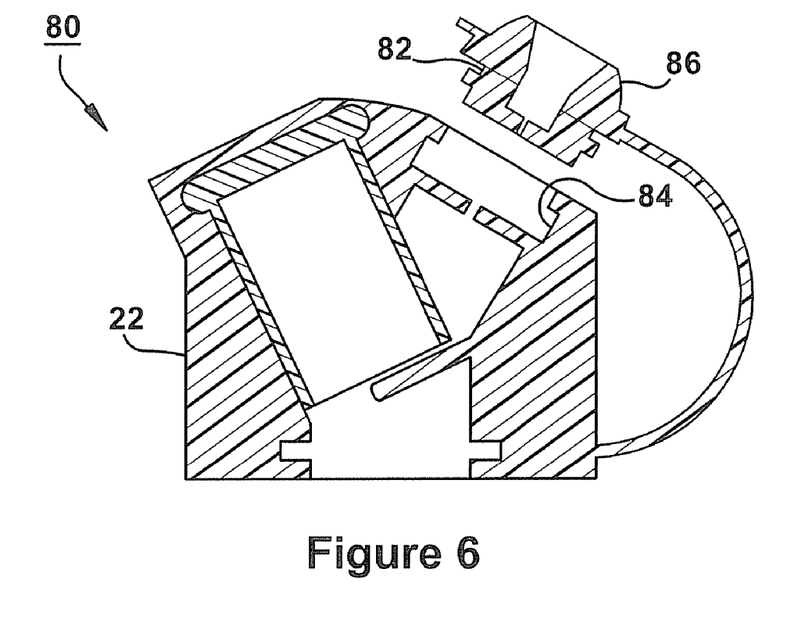
FIG. 6 is a cross-sectional view of a valve having a flip cap with a crowned top.

FIG. 6 shows a valve 80 having a flip cap 82 and a corresponding locking groove 84. The flip cap has a crowned top surface 86 to give it additional rigidity. The structure and size of the cap and associated locking reservoir on the valve body 22 is believed to permit devices to be inserted into and removed from the valve and that the cap itself to be substantial enough to remain successfully inserted.

Figure 7:
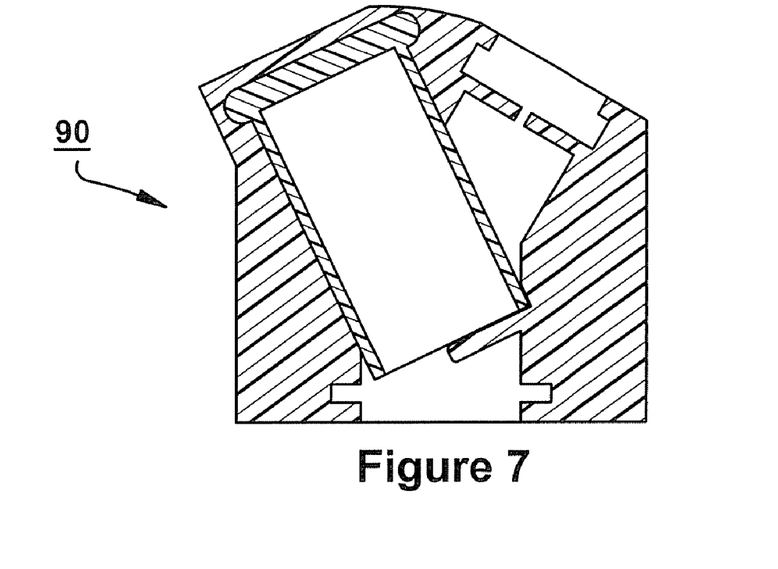
FIG. 7 is a cross-sectional view of a valve having an integral flap member but without an integral tether and flip cap.

FIG. 7 is a cross-sectional view of a valve 90 without an integrally molded tether or flip cap.

Figure 8A:
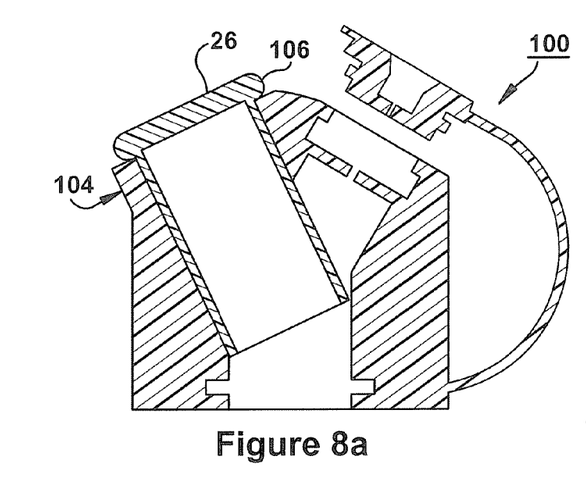
FIG. 8a is a cross-sectional view of a valve having a seal curtain inserted through an aperture on the top side of the body.
Figure 8B:
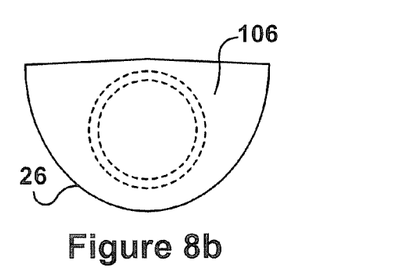
FIG. 8b is a top view of the seal curtain of FIG. 8a, showing a half-circle circumference of a seal curtain flange.
Figure 8C:
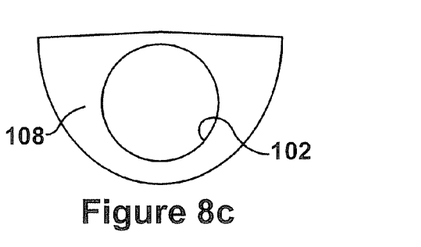
FIG. 8c is a top view of a portion of top surface of the body of FIG. 8a, showing a flange mounting surface.

Another embodiment of the invention is shown in FIGS. 8a, 8b, 8c and 9. In the orientation of a valve 100 shown in FIG. 8a, the seal curtain 26 is inserted into the cavity through an aperture 102 in the outer surface 104 of the body. FIG. 8b illustrates a larger sized semi-circular shaped flange 106 that can be pressed against a mounting surface 108 shown in FIG. 8c. Alternatively, the flange may be attached by an adhesive or any other suitable method. The illustrated structure created more area inside the cylindrical portion of the seal curtain for retaining fluids from the instrument inlet port 16, and also reduces the likelihood that the seal curtain can be detached.

Figure 9:
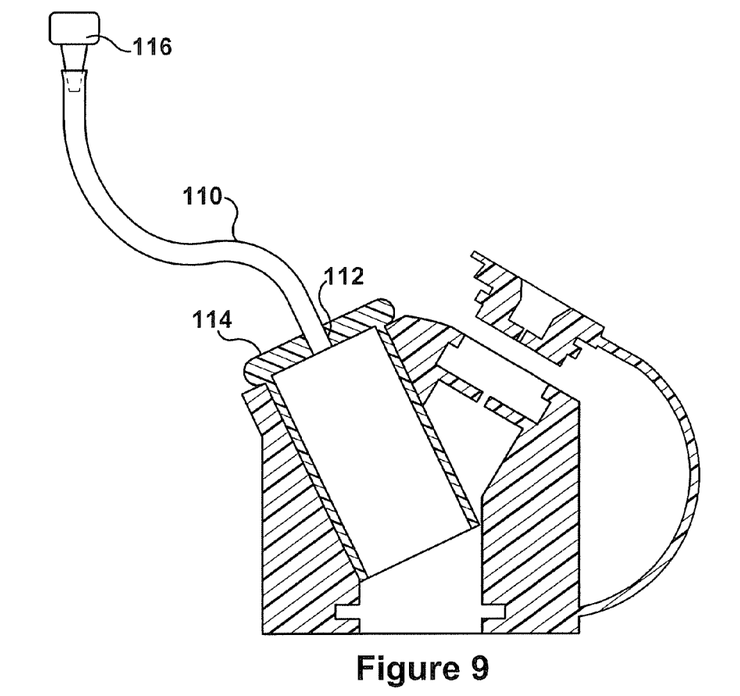
FIG. 9 is a plan view, partially in section, of a valve having a tube connected to an externally mounted seal curtain.

FIG. 9 shows the attachment of an inlet tube 110 to an aperture 112 in the lid 114. The proximal end of the tube has a check valve 116 that can be utilized be used to inject a viscous substance into the cylindrical portion of the seal curtain, such as for example, a water soluble lube. It is believed this material and others will improve the sealing capability of the device by restricting fluid flow from the instrument inlet port 16 and encourage the seal curtain and other thin membranes to cling to each other, which will also inhibit flow.

Figure 10A:
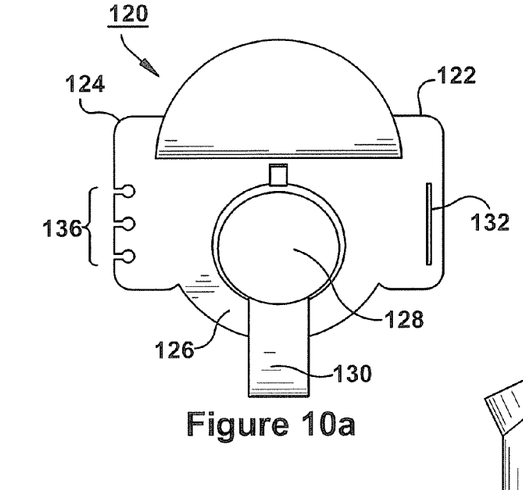
FIG. 10a is a top view of a valve having additional features for ease of guidewire use and storage.
Figure 10B:
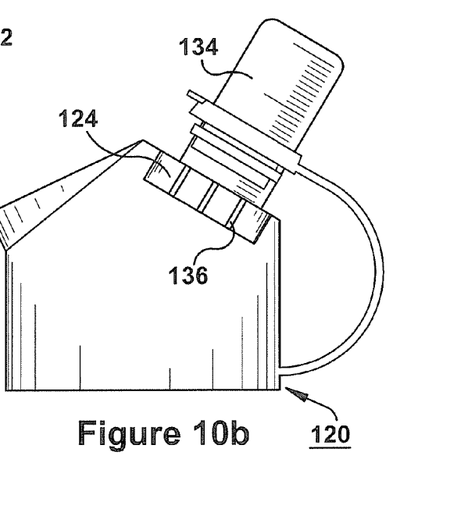

Two additional user-friendly features are illustrated in valve shown in FIGS. 10a-10b. FIG. 10a is a top view of a valve having two wings 122, 124 extending from opposing sides of a valve body 136. For perspective, a flip cap 128 integrally molded with a tether 130 is shown in an installed position. Each wing is integrally molded to the valve body as shown, but it should be understood in the practice of the invention that one or both or the wings could be separate adapters that are attached to the valve body.

Figure 10C:
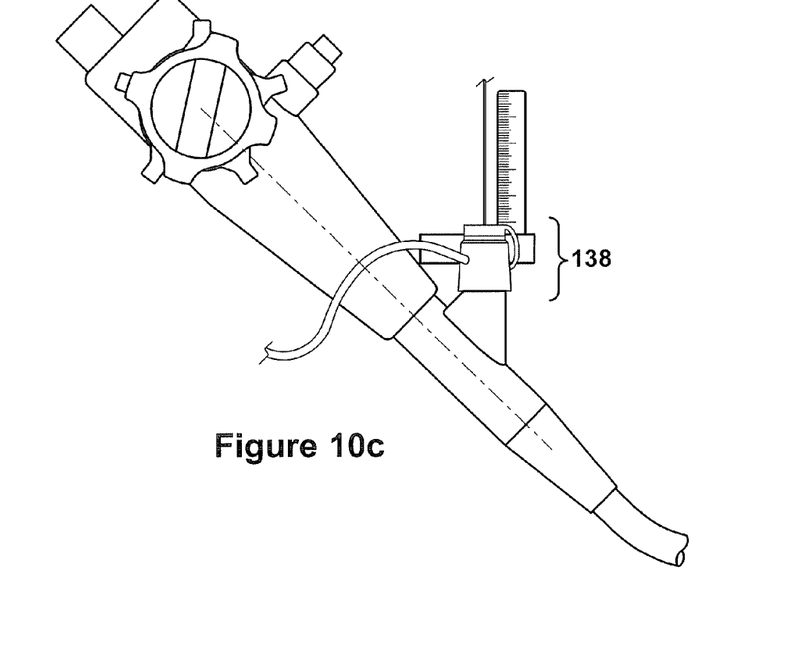

The first wing 122 includes a slot 132 sized for insertion of length measuring device, such as for example, a small metal ruler. In FIG. 10b, the slot 132 is on the far side of the valve 120 but a small scale 134 is shown in an installed position. The slot 132 is positioned such that the scale is oriented parallel to the inlet port of the valve 120. The ruler is useful to measure the depth insertion (or retraction) of a guidewire or other instrument used during certain endoscopic procedures. A photograph of a valve 138 with a measuring device during guidewire insertion is shown in FIG. 10c.

The second wing 124 also has a feature that is beneficial to a user when operating a guidewire. Guidewires can be up to 180" in length and are often used to reach locations within the GI tract that are other wise difficult to reach, such as for example, areas beyond the biliary duct. Thus, it is important to retain guidewire in a desired location so as to avoid re-insertion or loss of position in the event they are needed again. The wing 124 incorporates a plurality of wire engaging notches 136 for engagement of a guide wire. After insertion of the guidewire (not shown) into the endoscope to a desirable length, the proximal end of the guidewire can be looped in and out of the notches 136 to be held in place until needed. Three notches are shown, but it should be understood that notches of any number, size, shape or pattern can be used in the practice of the invention.

Figure 11:
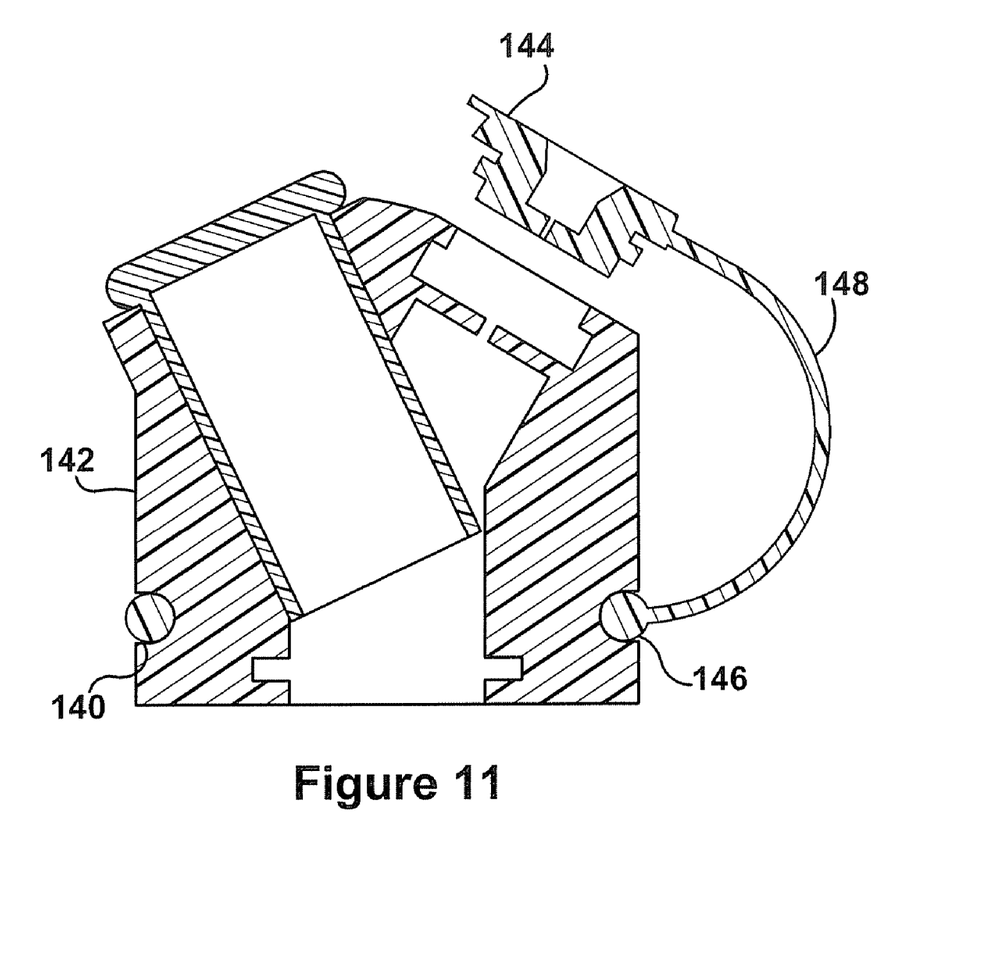
FIG. 11 is a cross-sectional view of a valve having a detachable tether and cap.

FIG. 11 shows another embodiment of the invention. In this case, a receptor groove 140 has been molded on the outside of the valve body 142. The flip cap 144 is attached to a ring 146 by a tether 148. The ring 146 is sized for insertion into the groove 140. The structure of the flip cap 144 allows it to be added to the valve during a subsequent assembly step. By breaking the valve into two constituent parts, the materials (and their associated physical properties) can be different so that the flexibility and responsiveness of the lid and slit can be independently optimized with respect to the valve body that can be enhanced to fit snugly on the endoscope instrument inlet port 16 and allow effective attachment of the lid during closure.

Figure 12A:
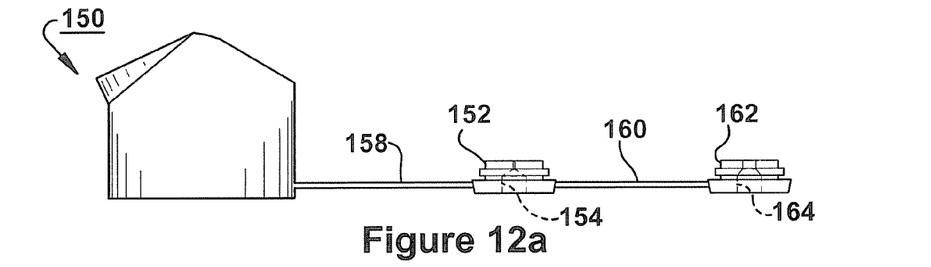
FIG. 12a is a plan view of a valve having two flip caps connected to the valve body by a single tether.
Figure 12B:
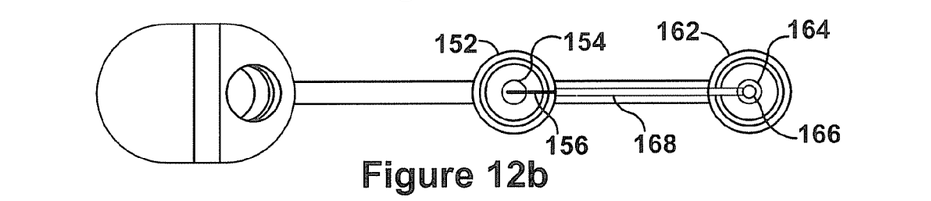

The flip cap assembly of a valve of this invention can be structured to include multiple flip caps each with an aperture therethrough. A valve 150 with such structure is shown in FIGS. 12a-12d. A first flip cap 152 includes a concave recess 154 leading to a narrow slit 156. A first tether portion 158 connects the first flip cap to the valve body, while a second tether portion 160 connects the first flip cap 152 to a second flip cap 164. The second flip cap 152 includes a concave recess 164 leading to an aperture 166 of reduced diameter. As shown in FIG. 12b, the second tether portion 160 includes a slot between the slit 156 and the aperture 166. The slit 156 and aperture 166 are of different size and shape. It should be obvious to one with ordinary skill in the art that the size, shape and orientation of either or both may vary in the practice of the invention.

Figure 12C:
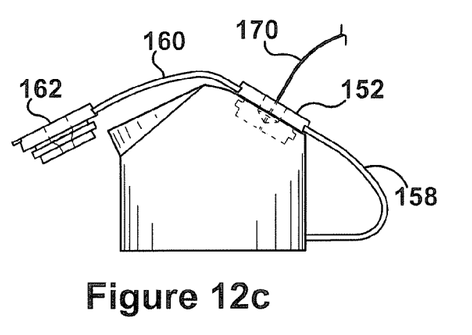
FIG. 12c is a plan view of the valve of FIG. 12a, showing a first flip cap having a smaller aperture therethrough installed into a valve entry port.
Figure 12D:
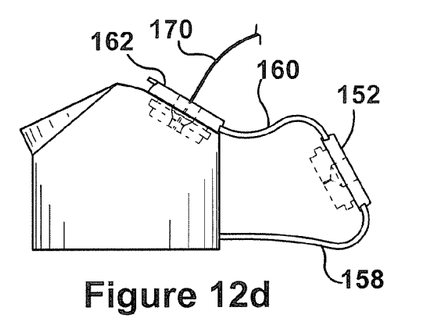
FIG. 12d is a plan view of the valve of FIG. 12a, showing a second flip cap having a larger aperture therethrough installed into a valve entry port.
Figure 13A:
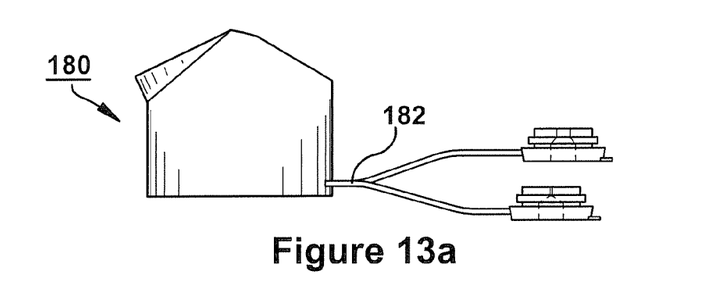
FIG. 13a is a plan view of a valve having two flip caps connected to the valve body by a single Y-shaped tether.
Figure 13B:
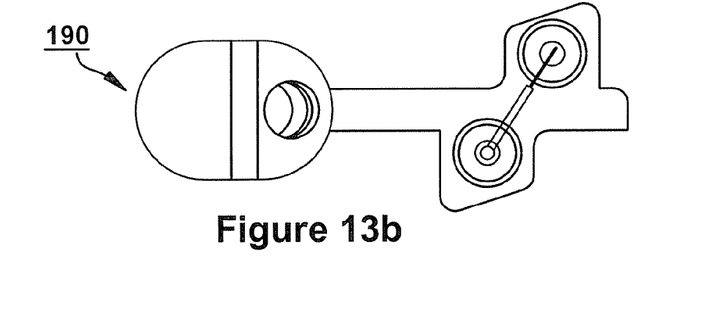
FIG. 13b is a top view of another valve having two flip caps connected to the valve body by a single tether.

The use of the valve 150 is shown in FIGS. 12c-12d. The first flip cap 152 is shown inserted into the inlet port of the valve 150 in FIG. 12c. A guidewire 170 is shown inserted through the slit 154. Anytime after the guidewire has been inserted to a desired length and it becomes necessary to inset a larger device into the valve 150, the slot 168 advantageously allows the guidewire 170 to traverse to the second flip cap 162. When it is necessary to insert the large device, the first flip cap 152 is opened and the guidewire is to the second flip cap 162 which is now closed. FIG. 12d shows the resulting orientation. As a result, large devices to be easily inserted through the larger hole 166 that has been designed to seal on bigger devices. In complimentary fashion, the slit 156 is designed and sized to seal on the guidewire and other smaller devices and avoids compromise by large device insertion. Two other exemplary multiple flip cap valves 180, 190 and shown in FIGS. 13a, 13b, respectively. The tether 182 of valve 180 is Y-shaped.

Figure 14A:
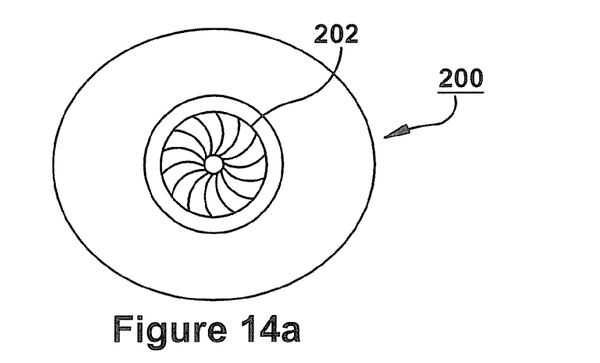
FIG. 14a is a top view of a sealing device having an adjustable inner diameter.
Figure 14B:
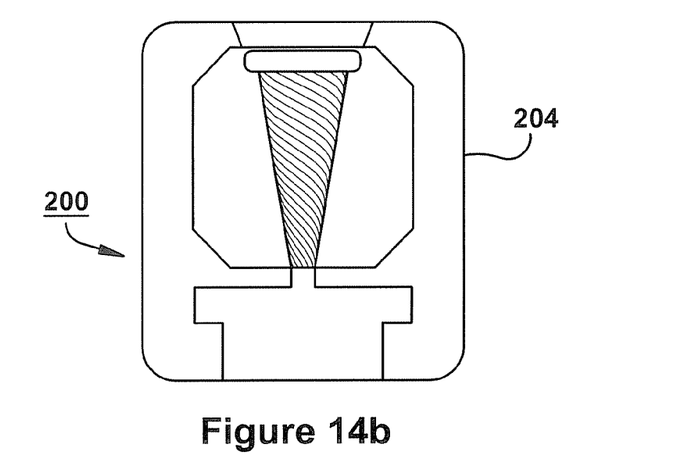

FIGS. 14a-14b are schematics that show another design that can improve the overall ability of the valve to create a seal and yet allow the insertion of larger diameter devices. The design includes an aperture that can be adjusted wider or narrower according to the size of the device being utilized. FIG. 14a is a top view of a sealing device having an adjustable inner diameter, and FIG. 14b is a cross-sectional view of the sealing device. The device 200 is position at or near the inlet port of a valve (not shown). An internal assembly 202 within a housing 204 adjusts to the device inserted. This type of fitting is commonly referred to as Touhy Burst fitting, and is well-known to those with ordinary skill in the art of catheter devices. The fitting 202 may be made to manually or automatically adjust to the diameter of the inserted device. For example, a tightening mechanism 62 is rotated about a central longitudinal axis, the tightening mechanism may be rotated to lock about any devices passing therethrough, such as for example, a guide wire. By rotating the tightening mechanism in an opposite direction, the seal is released.

Figure 15:
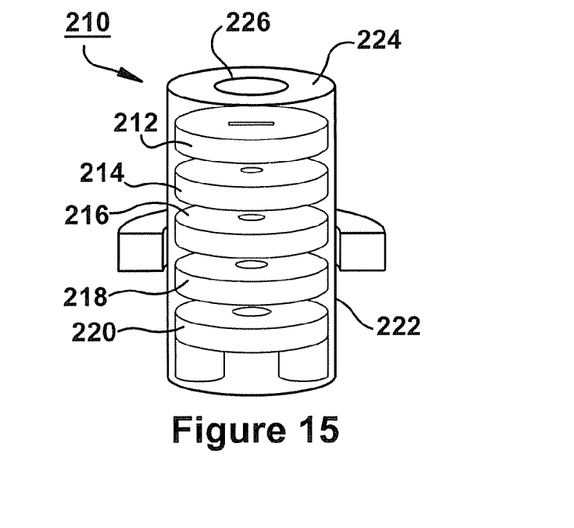
FIG. 15 is a schematic of a sealing device having stacked internal disks, each disk having an aperture therethrough.

FIG. 15 is a schematic of a sealing device 210 having stacked internal disks 212, 214, 216, 218, 220. Each disk has an aperture therethrough. The apertures may vary in size, shape and orientation from disk to disk as shown or in any other pattern. The device 210 utilizes a can-like outer shell 222 that captures the disks. The disks cooperate, along with air gaps in-between to diffuse the pressure from the scope, to accomplish the seal around an object inserted through an aperture 226 of a top surface 224 of the can 222.

It should be noted that these features described can be combined in a manner not specifically addressed in order to optimize the performance of the finished product.

While several embodiments of the invention has been illustrated and described, the present invention is not to be considered limited to the precise constructions disclosed. Various adaptations, modifications and uses of the invention may occur to those skilled in the arts to which the invention relates. It is the intention to cover all such adaptations, modifications and uses falling within the scope or spirit of the annexed claims.

What is claimed is:

1. A valve for providing sealable access to an instrument channel of an endoscope via an endoscope instrument inlet port, the valve comprising:
   a. a body having an open end adapted for connection to said instrument inlet port, interior walls defining a cavity, and an outer surface defining a valve entry port, wherein said cavity is Y-shaped having a main branch leading from said open end to two secondary branches, a first secondary branch open to said outer surface at said valve entry port and a second secondary branch, said secondary branch having a first branch end open to at least one of said main branch and said first secondary branch, and a second branch end opposite said first branch end;
   b. a flip cap removably connectable to said valve entry port having a slit therethrough; and
   c. a seal curtain having a flexible cylindrical portion, and a lid closing one end of said cylindrical portion, said seal curtain secured across said second secondary branch of said cavity with said lid distal from said first branch end;
   d. wherein at least a portion of said cylindrical portion of said seal curtain extends into said main branch to restrict fluid flow from said open end to said valve entry port, and flexibly permits instrument insertion from said valve entry port into said main branch.

2. The valve of claim 1 wherein a fluid may be dispensed through said valve entry port to irrigate said instrument channel.

3. The valve of claim 1 wherein a fluid may be dispensed through said slit to irrigate said instrument channel when said flip cap is connected to said valve entry port.

4. The valve of claim 1 wherein said valve entry port defines a downward flow path angled less than 90 degrees from a longitudinal axis of said body.

5. The valve of claim 1 wherein said body is constructed of a flexible plastic.

6. The valve of claim 1 wherein said valve entry port is sized for insertion of an endoscope instrument.

7. The valve of claim 1 wherein said seal curtain is inserted into said cavity through said open end.

8. The valve of claim 1 wherein said seal curtain is inserted into said cavity through an aperture in said outer surface of said body.

9. The valve of claim 8 wherein said seal curtain comprises a flange, wherein said flange is attached to said outer surface of said body.

10. The valve of claim 8 further comprising an inlet tube attached to an aperture in said lid for insertion of fluids into said cylindrical portion of said seal curtain.

11. The valve of claim 1 wherein said body comprises a wing having a slot sized for insertion of a length measuring device parallel to said channel.

12. The valve of claim 1 wherein said body comprises a wing having a plurality of wire engaging notches for engagement of a guide wire.

13. The valve of claim 1 wherein said flip cap is attached to a ring by a tether and said outer surface of said body defines a groove, wherein said ring is insertable into said groove.

14. The valve of claim 1 comprises a second flip cap, said second flip cap removably connectable to said valve entry port and having a second slit therethrough, wherein said second slit is not equal in size to said slit of said first flip cap.

15. The valve of claim 14 wherein said first flip cap and said second flip cap are attached to said body by a single tether.

16. The valve of claim 15 wherein said single tether is Y-shaped.

17. The valve of claim 15 wherein said first slit and said second slit are connected by a slot disposed within said single tether.

18. The valve of claim 1 wherein said slit comprises an aperture of adjustable diameter.

19. The valve of claim 1 further comprising a sealing assembly having a plurality of disks in a stacked orientation within an outer shell, each of said disks having an aperture therethrough.

20. The valve of claim 1 wherein said body further comprises a membrane within said first secondary branch, said membrane having a hole extending through a center thereof.

21. The valve of claim 1 wherein said second secondary branch terminates within said body prior to said outer surface.

* * * * *